(12) United States Patent
Loyen et al.

(10) Patent No.: US 7,700,124 B2
(45) Date of Patent: Apr. 20, 2010

(54) COSMETIC COMPOSITIONS COMPRISING A FINE AND POROUS POWDER

(75) Inventors: Karine Loyen, Pont-Audemer (FR); Sophie Kohler, Carrieres sur Seine (FR)

(73) Assignee: Arkema France, Colombes (FR)

( * ) Notice: Subject to any disclaimer, the term of this patent is extended or adjusted under 35 U.S.C. 154(b) by 432 days.

(21) Appl. No.: 11/268,967

(22) Filed: Nov. 8, 2005

(65) Prior Publication Data

US 2006/0115504 A1 Jun. 1, 2006

(30) Foreign Application Priority Data

Nov. 30, 2004 (FR) .................................. 04 12690

(51) Int. Cl.
*A61K 8/02* (2006.01)
*A61K 9/16* (2006.01)
*A61K 9/50* (2006.01)

(52) U.S. Cl. ...................... 424/401; 424/498

(58) Field of Classification Search ................ 424/401, 424/498

See application file for complete search history.

(56) References Cited

U.S. PATENT DOCUMENTS

| 4,831,061 | A | 5/1989 | Hilaire et al. |
| 4,927,860 | A | 5/1990 | Hilaire et al. |
| 2002/0010300 | A1 | 1/2002 | Mimoun |
| 2004/0265347 | A1 | 12/2004 | Auguste et al. |
| 2006/0127424 | A1* | 6/2006 | Asano et al. ............... 424/401 |

FOREIGN PATENT DOCUMENTS

| JP | 2001/220316 | 8/2001 |
| WO | WO 2004/043411 | 5/2004 |

* cited by examiner

*Primary Examiner*—Sreeni Padmanabhan
*Assistant Examiner*—Samira Jean-Louis
(74) *Attorney, Agent, or Firm*—Thomas F. Roland

(57) ABSTRACT

The invention is a water/oil emulsion including a porous powder, the particles of the powder having the following characteristics:
  an apparent specific surface of 1 to 299 $m^2/g$, measured by nitrogen absorption according to the ISO 9277 BET method;
  a linseed oil absorption of between 45 g/100 g of powder and 160 g/100 g of powder, measured according to ISO 787-5.

The mean diameter of the particles of the powder is between 2 μm and 100 μm, preferably from 2 to 50 μm, more advantageously still from 2 to 20 μm. The powder is chosen from a powder formed of polyamides, of polyesteramides, of polyurethanes, of poly(methyl methacrylate)s, of acrylic polymers, of polyesters, of silicones, of polyethylenes and of silicas. The invention further relates to the use of the emulsion for obtaining a make-up and/or care product for the skin which is nonshiny, nonoily, nonsticky and/or nontacky, as well as the use of the fine powder for improving the feel and/or the appearance of a cosmetic emulsion.

15 Claims, No Drawings

COSMETIC COMPOSITIONS COMPRISING A FINE AND POROUS POWDER

This application claims benefit, under U.S.C. §119 or §365 of French Application Number 04.12690, filed Nov. 30, 2004.

The present invention relates to cosmetic compositions used in the care and make-up field. These are emulsions mainly comprising an aqueous phase and a fatty phase and additionally comprising a fine and porous powder. The invention relates more particularly to care and/or make-up cosmetic compositions exhibiting a continuous fatty phase, it being possible for the latter to be composed of various types of volatile or nonvolatile oils of mineral, animal, vegetable or synthetic origin.

The use in these cosmetic compositions according to the invention of surfactants, of thickeners and more generally of surface-active agents makes it possible to obtain a stable dispersion of one phase in the other. It is also possible to have additives in these compositions, such as preservatives and fragrances but also cosmetic active agents, such as moisturizing agents (polyols), UV inhibitors, antiwrinkle agents, self-tanning agents, film-forming agents, antioxidants and many others.

Another subject-matter of the invention is a process for making up and/or caring for keratinous substances, such as the skin, lips, nails, hair, eyelashes, eyebrows or body hair of human beings, comprising the application to the keratinous substances of the composition according to the invention.

The composition according to the invention can be a composition for making up and/or caring for keratinous substances, in particular a composition for caring for the face (cream or fluid), a composition for caring for the body (moisturizing, slimming), a waterproof or non-waterproof sun cream composition, a composition for making up the skin, such as a foundation, an eyeshadow, a blusher or a concealer, or a product for making up the body. Make-up compositions generally comprise, on the one hand, a pulverulent phase comprising in particular pigments and fillers and, on the other hand, a fatty phase, the fillers and the fatty phase being intended to confer a degree of density on the finished product, to give softness and an emollient property to the make-up product and to promote its adhesion to the skin.

Compositions of continuous fatty phase type exhibit numerous advantages from the cosmetic and formulation viewpoint. The fatty phase according to the invention comprises solid or liquid fatty substances of vegetable, mineral, animal or synthetic origin. Mention may be made, for example, of esters, fatty alcohols, fatty acids or hydrocarbons comprising essentially carbon and hydrogen atoms and optionally nitrogen or oxygen atoms. This is because these formulations are advantageously compatible with the skin and its lipid constituents. The formation of a film at the surface of the skin contributes to limiting the evaporation of the water present in the layers of the skin and to keeping the latter moisturized, thus producing good protection of the skin with regard to desiccation. Mention may also be made of silicone oils and fluorinated oils.

Furthermore, as the active agents (moisturizing agents, chemical or physical UV screening agents) are generally lipophilic, they can be dispersed or dissolved more easily in the continuous fatty phase which will convey them to the constituent layers of the skin, providing good distribution of these active agents. The continuous and hydrophobic fatty phase can also constitute a protective medium for these active agents. This is because body fluids (tears, perspiration) or water have a tendency to remove these active agents from the surface of the skin by washing or runoff. The incompatibility of water with the continuous fatty phase prevents or greatly restricts this removal. This is particularly valuable for skin-protecting sun creams of waterproof type which have to retain their protective effectiveness with regard to UV radiation even after bathing.

However, cosmetic compositions comprising a continuous fatty phase very often cause annoyance on application which sometimes limits their use by consumers. This is because the continuous fatty film at the surface of the skin causes a tacky, oily and sticky feeling which is no longer accepted by today's consumers. Furthermore, the shiny and oily appearance is harmful to the cosmetic and aesthetic properties of these creams. The application of a make-up after the application of day or sun cream is rendered difficult because of this tacky effect, which interferes with the spreading of the make-up over the skin. The application of the make-up is thus disrupted, resulting in uneven areas occurring in the make-up. Furthermore, over time, the make-up displays poor hold and also displays transfer and loss of the colours.

It is known to add volatile oils, such as silicone oils, to reduce the oily, tacky and sticky aspect of these compositions comprising a continuous fatty phase but they do not act protectively in combination with a continuous fatty phase and they do not have humectant properties for the skin. Furthermore, the polyols generally added to the formulations for their humectant and moisturizing properties for the skin contribute an undesirable persistent sticky effect to the skin which augments that of the cosmetic oils of the composition.

It is thus important to manufacture a cosmetic composition which simultaneously responds to the sensory and aesthetic problem while fulfilling its protective role with regard to the skin, as mentioned above. A water/oil emulsion comprising a fine and porous powder according to the invention makes it possible to solve this technical problem. In particular, it significantly reduces the greasy and sticky effect contributed by the oils and/or polyols of cosmetic compositions.

Furthermore, according to the document EP 1 582 194 from Ube Industries, a cosmetic composition is known which comprises a cosmetic base, a fragrance and a powder formed of spherical, cylindrical or dumbbell-shaped polyamide (abbreviated to PA) particles. These particles are porous and have a mean diameter of 1 to 30 μm, a specific surface of 5 $m^2$/g or more, a linseed oil absorption of 200 ml/100 g or more, a crystallinity of 40% or more and a ratio of the volume-average diameter with respect to the number-average diameter of 1.0 to 1.5. The cosmetic compositions disclosed in this document preferably comprise from 3 to 10% by weight of fatty phase with respect to the total weight of the composition. The powder of these cosmetic compositions brings about a light scattering effect at the surface of the skin and has a high sebum absorption capacity, which prevents the appearance of greasy and shiny areas on the face.

The document FR 2 854 064 from L'Oreal relates to a make-up composition which can absorb sebum, making it possible to thus have available a make-up exhibiting good cosmetic properties over time, in particular exhibiting good hold with regard to rubbing actions, transfer-free properties, good homogeneity, maintenance of the initial colour of the make-up and absence of shininess (hold of the mattness). This composition comprises:
  a first sebum-absorbing powder having a BET specific surface (see below) of greater than or equal to 300 $m^2$/g, preferably of greater than 500 $m^2$/g, in combination with
  a second powder having a specific critical surface energy which is not impregnated with sebum and which prevents the latter from modifying the cosmetic properties of the make-up.

A subject-matter of the invention is a water/oil emulsion comprising a porous powder, the particles of the powder having the following characteristics:

an apparent specific surface of 1 to 299 $m^2/g$, measured by nitrogen absorption according to the ISO 9277 BET method;

a linseed oil absorption of between 45 g/100 g of powder and 160 g/100 g of powder, measured according to ISO 787-5.

According to one embodiment, the emulsion is characterized in that the powder exhibits a linseed oil absorption of 50 g/100 g of powder to 150 g/100 g of powder.

According to one embodiment, the emulsion is characterized in that the apparent specific surface is from 0.5 to 150 $m^2/g$.

According to one embodiment, the emulsion is characterized in that the apparent specific surface is from 0.5 to 100 $m^2/g$, advantageously from 0.5 to 50 $m^2/g$, more advantageously still from 0.5 to 40 $m^2/g$.

According to one embodiment, the emulsion is characterized in that the powder particles have a mean diameter ranging from 2 μm to 100 μm, preferably from 2 to 50 μm, more advantageously still from 2 to 20 μm.

According to one embodiment, the emulsion is characterized in that the powder particles have a spheroidal shape.

According to one embodiment, the emulsion is characterized in that the powder is chosen from a powder formed of polyamides, of polyesteramides, of polyurethanes, of poly(methyl methacrylate)s, of acrylic polymers, of polyesters, of silicones, of polyethylenes and of silicas.

According to one embodiment, the emulsion is characterized in that its composition is as follows:

10 to 75%, preferably 30 to 65%, of an aqueous phase;
0.1 to 30%, preferably 1 to 20%, of porous powder; and
89.9 to 24.9% of a fatty phase, the total forming 100%.

According to one embodiment, the emulsion is characterized in that the fatty phase comprises less than 25% (by weight with respect to the total composition) of volatile oil.

According to one embodiment, the emulsion is characterized in that the volatile oil is a silicone oil.

According to one embodiment, the emulsion is characterized in that the aqueous phase comprises from 10 to 60% of polyols.

Account to one embodiment, the emulsion is characterized in that it comprises a cosmetic ingredient chosen from antioxidants, fragrances, preservatives, neutralizing agents, surfactants, film-forming polymers, thickeners, ultraviolet radiation blockers, vitamins, colouring materials, emulsion stabilizers, moisturizing agents, self-tanning compounds, antiwrinkle active agents and their mixtures.

According to one embodiment, the emulsion is characterized in that it is a cream or a fluid for caring for the face, a moisturizing and/or slimming cream or fluid for caring for the body, a waterproof or nonwaterproof sun cream, a foundation, an eyeshadow, a blusher, a concealer or a product for making up the body.

The invention also relates to the use of an emulsion for manufacturing a make-up and/or care product for the skin which is nonshiny, nonoily, nonsticky and/or nontacky.

The invention also relates to a cosmetic process for making up and/or caring for keratinous substances comprising the application, to these substances, of an emulsion as described above.

A subject-matter of the invention is the use of a fine and porous powder exhibiting the following characteristics:

an apparent specific surface of 1 to 299 $m^2/g$, measured by nitrogen absorption according to the ISO 9277 BET method;

a linseed oil absorption of between 45 g/100 g of powder and 160 g/100 g of powder, measured according to ISO 787-5;

for improving the feel and/or the appearance of a water/oil cosmetic emulsion.

According to one embodiment, the use of the fine and porous powder is characterized in that the apparent specific surface of the said powder is from 0.5 to 150 $m^2/g$, measured by nitrogen absorption according to the ISO 9277 BET method.

According to one embodiment, the use of the fine and porous powder is characterized in that the powder particles have a mean diameter ranging from 5 to 20 μm.

According to one embodiment, the use of the fine and porous powder is characterized in that the powder particles have a spheroidal shape.

The invention will now be described in more detail.

Powder

As regards the powder formed of polyamide homopolymers or copolymers, the term "polyamide" is understood as meaning the condensation products:

of one or more amino acids, such as aminocaproic, 7-aminoheptanoic, 11-aminoundecanoic and 12-aminododecanoic acids;

of one or more lactams, such as caprolactam, oenantholactam, capryllactam and lauryllactam;

of one or more salts or mixtures of diamines, such as hexamethylenediamine, dodecamethylenediamine, meta-xylylenediamine, bis(p-aminocyclohexyl)methane and trimethylhexamethylenediamine, with diacids, such as isophthalic, terephthalic, adipic, azelaic, suberic, sebacic and dodecanedicarboxylic acids.

This term is also understood as meaning the fine powders obtained from a monomer which is a lactam which is converted directly to a fine polyamide powder.

Mention may be made, as examples of lactams, of those having from 3 to 12 carbon atoms in the main ring and which can be substituted. Mention may be made, for example, of β,β-dimethylpropiolactam, α,α-dimethyl-propiolactam, amylolactam, caprolactam, capryllactam and lauryllactam.

The method consists in suspending the lactam in an organic liquid or dissolving it in a solvent and in carrying out a polymerization of anionic type which makes it possible to directly obtain the PA powder, which separates by itself from the liquid medium as it is formed. The method for the anionic polymerization of lactams is based essentially on the use of a catalyst, such as sodium or one of its compounds, for example sodium hydride or sodium methoxide, and of an activator, such as N-carboxyanilide lactams, isocyanates, carbodiimides, cyanimides, acyllactams, triazines, ureas, N-substituted imides and esters, inter alia in the presence optionally of a finely divided inorganic or organic filler having a role of crystallization seed, such as PA, silica or talc powder, and in the presence of an N,N-alkylenebisamide, more particularly N,N'-ethylenebisstearamide, N,N'-ethylene-bisoleamide, N,N'-ethylenebispalmitamide, -gadoleamide, -cetoleamide and -erucamide, N,N'-dioleyldipamide and N,N'-dierucylamide. The process is disclosed in Patents EP 192 515 and EP 303 530.

Mention may be made, as examples of polyamides which can be used in the invention, of PA 6, PA 6, 6, PA 11 and PA 12.

Mention may be made, as PA powders, of:

nonspherical powders formed of polyamides 12 sold by various companies: Nylon 2159V and Nylon 2070V (Kobo), Covabead N12 and Covabead N12-10 (LCW), Vestosint 7010 BC, Vestosint 7020 BC and Vestosint 7040 BC (Degussa);

spherical powders formed of polyamides 12 sold by various companies: SP-500, S-501, SP10 (Toray), Ubesta (Ube), GPA 700 (Ganz Chemical);

porous spheroidal powders sold by Arkema under the Orgasol® name: Orgasol® 2002 UD NAT COS, Orgasol® 2002 EXD NAT COS, Orgasol® 2002 EXD NAT COS Type S, Orgasol® 2002 D NAT COS, Orgasol® 1002 D NAT COS and Orgasol® 1002 EXD BL10 COS, and under the impregnated Orgasol® name: Orgasol® 1002 BL10PX COS impregnated to 20% with octyl methoxycinnamate, Orgasol® 2002 N5PX COS impregnated to 20% with octyl methoxycinnamate, Orgasol® 2002 N5HY COS impregnated to 40% with a hyaluronic acid solution, Orgasol® N10S COS impregnated to 5% with dimethicone, Orgasol® 2002 N10VE COS impregnated to 12% with tocopheryl acetate and Orgasol® 2002 N10VB COS impregnated to 10% with D-panthenol.

As regards the copolyamides, mention may be made of the copolyamides resulting from the condensation of at least two $\alpha,\omega$-aminocarboxylic acids or of two lactams or of one lactam and of one $\alpha,\omega$-aminocarboxylic acid. Mention may also be made of the copolyamides resulting from the condensation of at least one $\alpha,\omega$-aminocarboxylic acid (or one lactam), at least one diamine and at least one dicarboxylic acid. Mention may also be made of the copolyamides resulting from the condensation of an aliphatic diamine with an aliphatic dicarboxylic acid and at least one other monomer chosen from aliphatic diamines other than the above and aliphatic diacids other than the above.

The lactams which can be used are the same as those mentioned above.

Mention may be made, as examples of $\alpha,\omega$-aminocarboxylic acids, of aminoundecanoic acid and aminododecanoic acid.

Mention may be made, as examples of dicarboxylic acids, of adipic acid, sebacic acid, isophthalic acid, butanedioic acid, 1,4-cyclohexanedicarboxylic acid, terephthalic acid, the sodium or lithium salt of sulphoisophthalic acid, dimerized fatty acids (these dimerized fatty acids have a dimer content of at least 98% and are preferably hydrogenated) and dodecanedioic acid $HOOC-(CH_2)_{10}-COOH$.

An example of a diamine can be an aliphatic diamine having from 6 to 12 atoms; it can be saturated cyclic and/or arylic. Mention may be made, as examples, of hexamethylenediamine, piperazine, tetramethylenediamine, octamethylenediamine, decamethylenediamine, dodecamethylenediamine, 1,5-diaminohexane, 2,2,4-trimethyl-1,6-diaminohexane, polyoldiamines, isophorone-diamine (IPD), methylpentamethylenediamine (MPDM), bis(aminocyclohexyl)methane (BACM) or bis(3-methyl-4-aminocyclohexyl)methane (BMACM).

Mention may be made, as examples of copolyamides, of copolymers of caprolactam and of lauryllactam (PA 6/12), copolymers of caprolactam, of adipic acid and of hexamethylenediamine (PA 6/6, 6), copolymers of caprolactam, of lauryllactam, of adipic acid and of hexamethylenediamine (PA 6/12/6, 6), copolymers of caprolactam, of lauryllactam, of 11-aminoundecanoic acid, of azelaic acid and of hexamethylenediamine (PA 6/6, 9/11/12), copolymers of caprolactam, of lauryllactam, of 11-aminoundecanoic acid, of adipic acid and of hexamethylenediamine (PA 6/6, 6/11/12), or copolymers of lauryllactam, of azelaic acid and of hexamethylenediamine (PA 6, 9/12).

Use may be made of blends of polyamide and/or of copolyamide. These are, for example, blends of aliphatic polyamides and of semiaromatic polyamides and blends of aliphatic polyamides and of cycloaliphatic polyamides.

The powders can be manufactured by any means, dissolution in and precipitation from an alcohol. Advantageously, the powders are produced by polymerization in a solvent, the powders being insoluble in this solvent (polymerization of anionic type defined above). Mention may be made of the process disclosed in EP 192 515 and EP 303 530.

Use may also be made of powders formed of copolyesteramides comprising, in moles (the total being 100%):

1 to 98% of a lactam, 1 to 98% of a lactone, and optionally 1 to 98% of another lactam, and which have a diameter of between 1 µm and 200 µm and a specific surface of between 1 and 25 $m^2/g$.

The lactams which can be used to manufacture the copolyesteramides are the same as those mentioned above. Use is advantageously made of caprolactam and lauryllactam.

Mention may be made, as examples of lactones, of caprolactone, valerolactone and butyrolactone. Use is advantageously made of caprolactone.

The process for the preparation of these copolyesteramide powders by anionic polymerization is disclosed in the document EP 1 172 396.

Use may also be made of powders formed of polyurethanes, of acrylic polymers, of polyesters, of silicones, of polyethylenes or of silicas.

Mention may be made, as silica powder, of:

porous silica microspheres sold under the name Silica Beads SB-700 by Myoshi or Sunsphere® H51 or Sunsphere® H33 by Asahi Glass;

amorphous silica microspheres coated with polydimethylsiloxane sold under the name SA Sunsphere® H33 or SA Sunsphere® H53 by Asahi Glass.

Mention may be made, as powder formed of acrylic polymers, of:

the poly(methyl methacrylate) powders sold under the name Covabead® LH85 by LCW;

the poly(methyl methacrylate/ethylene glycol dimethacrylate) powders sold under the name Dow Corning 5640 Microsponge® Skin Oil Adsorber by Dow Corning or Ganzpearl® GMP-0820 by Ganz Chemical;

the poly(allyl methacrylate/ethylene glycol dimethacrylate) powders sold under the name Poly-Pore® L200 or Poly-Pore® E200 by Amcol;

the ethylene glycol dimethacrylate/lauryl methacrylate copolymer powders sold under the name Polytrap® 6603 by Dow Corning.

Mention may be made, as silicone elastomer powder, of the powders sold under the names Trefil® Powder E-505C or Trefil® Powder E-506C by Dow Corning.

Advantageously, the powder particles have a spheroidal shape.

Fatty Phase

A fatty phase can comprise a liquid fatty phase and optionally a solid fatty phase (such as waxes). The liquid fatty phase can comprise one or more oils which are liquid at ambient temperature (25° C.); these oils are volatile or nonvolatile. The liquid fatty phase is formed of hydrocarbon oils, indeed even optionally of silicone oils.

The fatty phase of the composition is a continuous fatty phase which, with the water, provides an emulsion in the water-in-oil form. This fatty phase comprises one or more oils, that is say water-immiscible fatty substances. These volatile or nonvolatile oils are of mineral, animal, vegetable or synthetic origin and can be hydrocarbon, silicone or fluorinated oils. The term "hydrocarbon oil" is understood to mean an oil formed essentially, indeed even composed, of carbon and hydrogen atoms and optionally of oxygen or nitrogen atoms. It can comprise alcohol, ester, ether, carboxylic acid, amine and/or amide groups.

It can comprise one or more oils which are liquid at ambient temperature (25° C.), preferably at least one nonvolatile liquid oil. The term "nonvolatile liquid oil" is understood to mean an oil which is capable of remaining on the skin at ambient temperature (25° C.) and atmospheric pressure for at least one hour and which has in particular a nonzero vapour pressure at ambient temperature (25° C.) and atmospheric pressure of less than or equal to 0.01 mmHg (1.33 Pa).

The liquid fatty phase advantageously comprises one or more nonvolatile oils which provide an emollient effect on the skin. Mention may be made of fatty esters, such as cetearyl isononoate, isotridecyl isononoate, isostearyl isostearate, isopropyl isostearate, isopropyl myristate, isopropyl palmitate, butyl stearate, hexyl laurate, isonononyl isononoate, 2-ethylhexyl palmitate, 2-hexyldecyl laurate, 2-octyldecyl palmitate, 2-octyldodecyl myristate or lactate, di(2-ethylhexyl) succinate, diisostearyl malate, glyceryl or triglyceryl triisostearate, or tocopheryl acetate, higher fatty acids, such as myristic acid, palmitic acid, stearic acid, behenic acid, oleic acid, linoleic acid, linolenic acid or isostearic acid, caprylic/ capric acid triglyceride, higher fatty alcohols, such as oleyl alcohol, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, hexyl laurate and their mixtures. They can be mineral oils: hydrocarbon oils, such as liquid paraffin, squalane, liquid petrolatum and their mixtures.

The composition optionally comprises nonvolatile silicone oils, such as, for example, dimethylsiloxanes.

The liquid fatty phase can also optionally comprise volatile oils. The term "volatile oil" is understood as meaning an oil capable of evaporating from the skin in less than one hour at ambient temperature and atmospheric pressure. This oil has in particular a vapour pressure at ambient temperature (25° C.) and atmospheric pressure (760 mmHg) of greater than 0.01 and less than or equal to 300 mmHg (1.33 Pa to 40 000 Pa) and preferably ranging from 0.05 to 300 mmHg (6.65 Pa to 40 000 Pa).

The volatile oils are chosen, for example, from silicone oils which contribute to reducing the greasy effect of formulations with a continuous fatty phase. Mention may be made of linear or cyclic silicone oils having a viscosity at ambient temperature of less than 8 mm$^2$/s and having in particular from 2 to 7 silicon atoms, these silicones optionally comprising alkyl or alkoxy groups having from 1 to 10 carbon atoms. Mention may be made, as volatile silicone oil which can be used in the invention, of in particular octamethylcyclotetrasiloxane, decamethyl-cyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane, dodecamethylpentasiloxane and their mixtures.

They are more particularly from the family of the polyalkyl- or polyarylsiloxanes: cyclomethicone (DC 345 from Dow Corning), caprylyl methicone or cyclopentasiloxane (DC245 from Dow Corning).

Mention may also be made of volatile hydrocarbon oils having from 8 to 16 carbon atoms and their mixtures and in particular branched $C_8$ to $C_{16}$ alkanes, such as $C_8$ to $C_{16}$ isoalkanes (also referred to as isoparaffins), isododecane, isodecane, isohexadecane, branched $C_8$ to $C_{16}$ esters, such as isohexyl neopentanoate, and their mixtures.

Advantageously, the composition according to the invention comprises at most 25% of volatile oil and in particular of volatile silicone oil, preferably at most 15% (% by weight with respect to the total composition).

Aqueous Phase

The aqueous phase comprises water. The latter can be a floral water, such as cornflower water, and/or a mineral water, such as water from Vittel, water from Lucas or water from La Roche Posay, and/or a thermal water. The aqueous phase can also comprise water-miscible constituents, such as, for example, primary alcohols, such as ethanol and isopropanol, polyols, such as glycols added for their humectant properties: glycerol, propylene glycol, butylene glycol, dipropylene glycol or diethylene glycol, glycol ethers, such as mono-, di- or tripropylene glycol or mono-, di- or triethylene glycol ($C_1$-$C_4$)alkyl ethers, and their mixtures.

The aqueous phase can additionally comprise stabilizing agents, such as sodium chloride, magnesium dichloride and magnesium sulphate.

The aqueous phase can also comprise any water-soluble or water-dispersible compound compatible with an aqueous phase, such as gelling agents, film-forming polymers, thickeners, surfactants and their mixtures.

Other Compounds

The cosmetic composition according to the invention can also comprise surfactants (generally lipophilic) of anionic, nonionic or amphoteric type which facilitate the dispersion of the aqueous phase in the fatty phase, so as to obtain a stable water/oil emulsion, or additives, such as preservatives (generally hydrophilic), fragrances (generally lipophilic), fillers other than the powder according to the invention, colouring materials (pigments, soluble dyes), thickeners (waxes, gelling agents), emulsion stabilizers (generally hydrophilic) or chelating agents (generally hydrophilic).

The surfactants can be of ester type, such as sorbitan derivatives (e.g., sorbitan sesquiisostearate) or methyl glucose isostearate. They can be of polymer type, such as PEG-45/dodecyl glycol copolymer. They can also be silicone surfactants suitable for the emulsification of silicone oils: they are, for example, dimethicone copolyols, such as PEG/PPG-18/18 dimethicone, sold by Dow Corning under the name DC5225C.

The thickeners can, for example, be soluble in the fatty phase in order to adjust its consistency or to contribute to the stability of the composition: mention may be made, for example, of candelilla wax or silicone gums or elastomers (DC1411 and DC9040 from Dow Corning).

The preservatives are mixtures of paraben derivatives and/ or of phenoxyethanol.

Mention may be made, for example, of EthyleneDiamine-TetraAcetic (EDTA) as chelating agent.

They can also comprise cosmetic active agents which improve the human keratinous substances mentioned above. The cosmetic active agents comprise moisturizing agents (generally hydrophilic), such as polyols, UV radiation blockers, such as organic screening agents (generally lipophilic) or inorganic particles, such as $TiO_2$ or $ZnO$, which may or may not be surface treated, antiwrinkle active agents (generally hydrophilic), self-tanning agents (generally hydrophilic), film-forming agents (lipophilic or hydrophilic, depending on their nature) or antioxidants (lipophilic or hydrophilic, depending on their nature).

Mention may be made, as inorganic screening agents, of dispersions of ZnO and of $TiO_2$ in mixtures of silicone oils.

The cosmetic composition according to the invention advantageously comprises:
- 10 to 75%, preferably from 30 to 65%, of aqueous phase;
- 0.1 to 30%, preferably from 1 to 20%, of powder according to the invention; and
- 89.9 to 24.9% of fatty phase, the total forming 100% (% by weight).

For its part, the aqueous phase preferably comprises 10 to 60% of polyols with respect to the total aqueous phase.

Furthermore, it can comprise 0.5 to 10%, preferably 3 to 5%, of surfactants, 0.01 to 2% of additives and 0.005 to 10% of cosmetic active agents, with respect to the total composition.

The characteristics of the powders of the composition which is a subject-matter of the invention are:
1. the very fine size of the particles, from 2 μm to 100 μm, preferably from 2 to 50 μm, more advantageously still from 2 to 20 μm,
2. the narrow particle size distribution. The particle size distribution of the powders is determined according to the usual techniques, for example using a Coulter Multisizer II particle sizer, according to Standard ISO 13319. It is possible, from the particle size distribution, to determine the mean diameter and the particle size dispersion (standard deviation), which measures the narrowing of the distribution. This is one of the advantages of the process described, which makes it possible to obtain a narrow distribution with a standard deviation of between 1 and 3 μm, indeed even often of less than 2 μm.
3. the advantageously spheroidal shape of the particles, that is to say in the form of a spheroid, which means: approximately spherical solid.
4. the surface porosity, characterized by the apparent specific surface (ASS) of the powders, from 0.5 to 299 $m^2/g$, preferably from 0.5 to 150 $m^2/g$, more preferably still from 0.5 to 100 $m^2/g$, advantageously from 0.5 to 50 $m^2/g$, more advantageously still from 0.5 to 40 $m^2/g$, measured by nitrogen absorption according to the BET method defined below.
5. a linseed oil absorption between 45 g/100 g and 160 g/100 g, preferably between 50 g/100 g and 150 g/100 g, measured according to the method defined below.

The characteristics listed above contribute strongly to the soft feel and to the achievement, after application, of the matt and powdered appearance of the composition, are involved in the absorption of a portion of the fatty phase and contribute to limiting the negative effects of the said fatty phase (greasy, oily, sticky feeling).

The apparent specific surface ASS is determined according to the BET (Brunauer-Emmet-Teller) method described in International Standard ISO 9277. The BET specific surface corresponds to the total specific surface (thus including micropores) of the powder.

The method for the uptake of linseed oil or absorption of linseed oil by a powder is described in Standard ISO 787-5. It corresponds to the amount of oil adsorbed on the available surface of the powder. An amount w (in grams) of powder of between approximately 0.5 g and 5 g is placed in a glass beaker and then linseed oil is added dropwise. After addition of 4 to 5 drops, the oil is incorporated in the powder using a spatula and the addition of the oil is continued until conglomerates of oil and of powder are formed. From this moment, the oil is added at the rate of one drop at a time and the mixture is subsequently triturated with a spatula. The addition of the oil is halted when a solid ball is obtained. The weight w' (expressed in g) of the oil used is then recorded. The linseed oil uptake or linseed oil absorption is expressed as w'/w (g of oil/g of powder) and is subsequently converted to g/100 g of powder.

The examples in TABLES 1 TO 4 below are defined in the following way:
1. Powder 1: Orgasol® 2002EXD NAT COS, that is to say PA 12 powder, size of the particles 10 μm, ASS 4+/−1.5 $m^2/g$, linseed oil uptake of 79 g/100 g.
2. Powder 2: Orgasol® 2002D NAT COS, PA 12 powder, size of the particles 20 μm, ASS 1.5+/−1 $m^2/g$, linseed oil uptake of 54 g/100 g.
3. Powder 3: Orgasol® 1002D NAT COS, PA 6 powder, size of the particles 20 μm, ASS 2.5+/−1 $m^2/g$, linseed oil uptake of 64 g/100 g.
4. The CONTROL composition does not comprise powder.

The percentages below are expressed by weight with respect to the total composition.

The nature of the compositions comprising powders 1 to 3 is defined below for each table.

The effect of the addition of PA powders according to the invention to emulsions comprising a continuous fatty phase was measured by sensory analysis in various types of compositions. Each composition was the subject of a sensory profile study carried out by a panel of five experts according to the following specifications:
- during the phase of application of the product: the greasiness, the oiliness, the speed of penetration;
- immediately after application: the shininess of the skin, the softness of the skin, the greasy skin effect, the tacky skin effect, the residue left by the cream on the skin.

Each composition was analysed under blind conditions by comparison of all the tests forming a series.

The results are collated in TABLES 1 to 4. The various criteria were evaluated on a scale ranging from 0 to 8, the value 0 indicating the absence of the criterion denoted (for example, a feeling of absence of greasiness), the value 8 indicating a very marked tendency for the criterion chosen (for example, a very great feeling of presence of greasiness).

Compositions A to C and Control 1 in TABLE 1 are compositions of water-in-silicone emulsion type comprising a high content of glycerol, for example corresponding to day cream compositions.

The process for the preparation of the compositions below consists in (i) combining the aqueous phase, (ii) combining the fatty phase, (iii) slowly adding the aqueous phase to the fatty phase while vigorously stirring, so as to form an emulsion, and then (iv) slowly adding the powder (except for the control) while gently stirring.

| Control 1 and Compositions A to C | | |
|---|---|---|
| Medium | % | Ingredients/Supplier |
| Aqueous phase | q.s. for 100 | Demineralized water |
| | 27.0 | Glycerol |
| | 13.5 | Butylene glycol |
| | 1.0 | NaCl |
| Fatty phase | 9.0 | DC 5225 C (1) (cyclopentasiloxane and PEG/PPG-18/18 dimethicone) |
| | 1.0 | DC 9040 (1) (cyclomethicone and dimethicone copolymers) |
| | 8.0 | DC 345 (1) (cyclomethicone) |
| | 3.5 | DC 1411 (1) (cyclomethicone and |

-continued

Control 1 and Compositions A to C

| Medium | % | Ingredients/Supplier |
|---|---|---|
| | | dimethicone) |
| | 2 | Silcare 41M15 (2) (caprylyl methicone) |
| Powder | x | Powder 1 to 3 according to Compositions A to C |

(1) Dow Corning;
(2) Clariant
Control 1: x = 0% of powder
Composition A: x = 3.5% of powder 1
Composition B: x = 3.5% of powder 2
Composition C: x = 3.5% of powder 3

TABLE 1

| | | Control 1 | Composition A | Composition B | Composition C |
|---|---|---|---|---|---|
| Behaviour during application | Greasiness | 8 | 3 | 2 | 5 |
| | Oiliness | 8 | 3 | 2 | 5 |
| | Speed of penetration | 0 | 4 | 5.5 | 2 |
| Behaviour after application | Shininess | 8 | 4 | 2 | 5 |
| | Softness | 2 | 4 | 7 | 5 |
| | Greasy skin | 8 | 6 | 2 | 5 |
| | Tacky skin | 7 | 5 | 1 | 5 |
| | Residue | 8 | 5 | 1 | 5 |

Compositions D to G and Control 2 in TABLE 2 are compositions of water-in-silicone emulsion type which can correspond, for example, to gentle moisturizing fluids.

The process for the preparation of the compositions below consists in (i) combining the preservatives at 60° C. (referred to as aqueous phase 2) and in adding them to the aqueous phase (referred to as aqueous phase 1), in (ii) combining the fatty phase while stirring with a Rayneri device in a cold bath, in (iii) slowly adding, with stirring, the aqueous phase 1+aqueous phase 2 mixture prepared in (i) to the fatty phase prepared in (ii), and in then (iv) slowly adding the powder (except for the control) while gently stirring.

Control 2 and Compositions D to G

| Medium | % | Ingredients/Supplier |
|---|---|---|
| Aqueous phase 1 | q.s. for 100 | Demineralized water |
| | 2.0 | NaCl |
| Aqueous phase 2 | 0.6 | Phenonip (phenoxyethanol and methylparaben and ethylparaben and butylparaben and propylparaben and isobutylparaben) (1) |
| | 0.2 | Chlorphenesin (2) |
| | 8.0 | Glycerol |
| Fatty phase | 10.0 | DC 5225 C (cyclopentasiloxane and PEG/PPG-18/18 dimethicone) (3) |
| | 10.0 | DC 345 (cyclomethicone) (3) |
| | 10.0 | DC 245 (cyclomethicone or cyclopentasiloxane) (3) |
| Powder | x | Powder 1 to 3 according to Compositions D to G |

(1) Clariant;
(2) Arnaud;
(3) Dow Corning
Control 2: x = 0% of powder
Composition D: x = 3.5% of powder 1
Composition E: x = 10% of powder 1
Composition F: x = 3.5% of powder 2
Composition G: x = 3.5% of powder 3

TABLE 2

| | | Control 2 | Composition D | Composition E | Composition F | Composition G |
|---|---|---|---|---|---|---|
| Behaviour during application | Oiliness | 7 | 2.5 | 0 | 7 | 3 |
| | Speed of penetration | 1 | 5 | 7 | 1 | 5 |
| Behaviour after application | Shininess | 4 | 1 | 0 | 4 | 1 |
| | Softness | 2 | 7 | 8 | 4 | 6 |

The addition of 1 to 30% by weight, preferably of 2 to 10%, of PA powders to a water-in-silicone emulsion (day cream, moisturizing fluid, body milk, aftershave care type, inter alia) makes it possible to significantly reduce the feeling of greasiness and of stickiness after application to the skin. Furthermore, after application, the shiny and oily appearance of the skin is completely suppressed.

The addition of powder even makes it possible, on the contrary, to obtain a matt and powdered appearance and confers a soft feel on the skin.

In particular, in a composition of the control 1 type comprising a high content of polyol (more than 50% of the aqueous phase) and a high content of nonvolatile silicone compounds (more than 50% of the fatty phase), the addition of powder reduces the feeling of greasiness and the residual tackiness on the skin.

In particular, in a composition of the control 2 type comprising polyols and volatile silicones, the addition of PA powder makes it possible to suppress the greasy effect associated with the silicone oils and with the polyols during application. This also makes it possible, after application, to obtain a powdered finish and a soft feeling, despite the evaporation of the volatile silicone oils, whereas, in the absence of the powder according to the invention, an unpleasant effect is obtained.

Compositions H to J and Control 3 in TABLE 3 are compositions of water-in-oil emulsion type. These compositions correspond, for example, to waterproof sun cream formulations.

The process for the manufacture of the formulation below consists in (1) mixing the constituents of the aqueous phase while heating at 0° C. and in (2) mixing the constituents of the fatty phase (referred to as fatty phase 1) while heating at 0° C. The thickener (referred to as fatty phase 2) and the sunscreen agents are subsequently added to the fatty phase maintained at 0° C. Finally, the aqueous phase is added to the fatty phase while stirring under shearing conditions, in order to obtain the emulsion. The emulsion is subsequently cooled to ambient temperature and the polyamide powder is dispersed in the emulsion with gentle stirring.

Control 3 and Compositions H to J

| Medium | % | Ingredients/Supplier |
|---|---|---|
| Aqueous phase | q.s. for 100 | Demineralized water |
| | 0.70 | Magnesium sulphate (1) |
| | 0.10 | EDETA BD (disodium EDTA) (2) |
| | 5.00 | Glycerol |
| Fatty phase 1 | 3.50 | Isolan IS (methyl glucose isostearate) (3) |
| | 1.00 | Elfacos ST9 (PEG-45/dodecyl glycol copolymer) (3) |
| | 11.00 | Cetiol A (hexyl laurate) (4) |
| | 5.00 | Cetiol SN (cetearyl isononanoate) (4) |
| | 10.00 | Cetiol S (diethylhexylcyclohexane) (4) |
| | 3.00 | Abil Soft AF100 (methoxy PEG/PPG-7/3/aminopropyl dimethicone) (3) |
| | 0.50 | Candelilla wax (4) |

-continued

Control 3 and Compositions H to J

| Medium | % | Ingredients/Supplier |
|---|---|---|
| | 0.80 | Phenonip (phenoxyethanol and methylparaben and ethylparaben and butylparaben and propylparaben and isobutylparaben) (5) |
| | 0.28 | Chlorphenesin (6) |
| | 0.20 | Butylparaben (5) |
| | 0.15 | Dehydroacetic acid (7) |
| | 1.00 | PVP/Eicosene copolymer (Antaron V-220) (8) |
| Fatty phase 2 | 1.50 | Disteardimonium hectorite (Bentone 38VCG) (4) |
| Inorganic screening agents | 2.50 | Zinc oxide + triethoxycaprylylsilane (Z Cote HP1) (2) |
| | 14.00 | Titanium dioxide (and) isononyl isononanoate (and) stearic acid (and) aluminium hydroxide (Kobo IN60S4) (9) |
| Powder | x | Powder 1 to 3 according to Compositions H to J |

(1) Merck,
(2) Laserson,
(3) Goldschmidt,
(4) Saci,
(5) Clariant,
(6) Arnaud,
( ) Sigma,
(8) IPS,
(9) Kobo
Control 3: x = 0% of powder
Composition H: x = 3.5% of powder 1
Composition I: x = 3.5% of powder 2
Composition J: x = 3.5% of powder 3

TABLE 3

| | | Control 3 | Composition H | Composition I | Composition J |
|---|---|---|---|---|---|
| Behaviour during application | Greasiness | 7 | 6 | 4 | 3 |
| | Oiliness | 7 | 6 | 4 | 3 |
| | Speed of penetration | 0 | 1 | 2 | 3 |
| Behaviour after application | Shininess | 7 | 6 | 5 | 4 |
| | Softness | 2 | 4 | 5 | 6 |
| | Greasy skin | 7 | 6 | 5 | 4 |
| | Tacky skin | 2 | 2 | 0 | 0 |
| | Residue | 7 | 7 | 3 | 2 |

Likewise, the addition of 1 to 30% by weight, preferably of 2 to 10%, of PA powders to a water-in-oil emulsion (waterproof sun cream type) makes it possible to significantly reduce the feeling of greasiness and of stickiness after application to the skin. Furthermore, after application, the white appearance of the skin due to the physical sunscreen agents (zinc oxide, titanium dioxide) is considerably toned down.

Compositions D and E and Control 2 are described above.

TABLE 4

| | Control 2 | Composition D | Composition E | Non-spheroidal polyamide powder* 3.5% |
|---|---|---|---|---|
| Softness after application | 2 | 7 | 4 | 2 |

*PA powder comprising nonspheroidal particles which is composed of angular grains of variable sizes, mean size 8 μm, and with an ASS of 4 m²/g.

Advantageously, an improvement in the softness of the skin is observed after application of the cream to the latter by virtue of the presence of the fine spheroidal powder in the composition according to the invention.

The invention claimed is:

1. A water/oil cosmetic emulsion having an improved feel and/or appearance comprising as the sole polyamide powder in said emulsion a fine and porous polyamide powder exhibiting the following characteristics:
    an apparent specific surface of 0.5 to 299 m²/g, measured by nitrogen absorption according to the ISO 9277 BET method;
    a linseed oil absorption of between 45 g/100 g of powder and 160 g/100 g of powder, measured according to ISO 787-5, and wherein said polyamide powder particles have a spheroidal shape.

2. The water/oil cosmetic emulsion of claim 1, wherein the apparent specific surface of the said powder is from 0.5 to 150 m²/g, measured by nitrogen absorption according to the ISO 9277 BET method.

3. The emulsion according to claim 1, wherein the apparent specific surface is from 0.5 to 100 m²/g.

4. The emulsion according to claim 1, wherein the powder exhibits a linseed oil absorption 50 g/100 g of powder to 150 g/ 100 g of powder.

5. The emulsion according to claim 1, wherein said polyamide is selected from the group consisting of PA 6, PA 6-6, PA 11 and PA12.

6. The emulsion according to claim 1, wherein the powder particles have a mean diameter ranging from 2 μm to 100 μm.

7. The water/oil cosmetic emulsion of claim 6 wherein the powder particles have a mean diameter ranging from 5 to 20 μm.

8. The emulsion according to claim 1, wherein its composition is as follows:
    10 to 75%, of an aqueous phase;
    0.1 to 30%, of porous powder; and
    89.9 to 24.9% of a fatty phase, the total forming 100%.

9. The emulsion according to claim 8, wherein its composition is as follows:
    30 to 65%, of an aqueous phase;
    1 to 20%, of porous powder; and
    89.9 to 24.9% of a fatty phase, the total forming 100%.

10. The emulsion according to claim 8, wherein the aqueous phase comprises from 10 to 60% of polyols.

11. The emulsion according to claim 8, wherein the fatty phase comprises less than 25% (by weight with respect to the total composition) of volatile oil.

12. The emulsion according to claim 11, wherein the volatile oil is a silicone oil.

13. The emulsion according to claim 1, comprising a cosmetic ingredient selected from the group consisting of antioxidants, fragrances, preservatives, neutralizing agents, surfactants, film-forming polymers, thickeners, ultraviolet radiation blockers, vitamins, colouring materials, emulsion stabilizers, moisturizing agents, self-tanning compounds, antiwrinkle active agents and their mixtures.

14. The emulsion according to claim 1, comprising a cream or a fluid for caring for the face, a moisturizing and/or slimming cream or fluid for caring for the body, a waterproof or nonwaterproof sun cream, a foundation, an eyeshadow, a blusher, a concealer or a product for making up the body.

15. The water/oil cosmetic emulsion of claim 1 wherein said water/oil emulsion comprises a make-up and/or care product for the skin which is nonshiny, nonoily, nonsticky and/or nontacky.

* * * * *